United States Patent [19]

Harris

[11] Patent Number: 4,721,118

[45] Date of Patent: Jan. 26, 1988

[54] PERVENOUS ELECTRICAL PACING LEAD WITH FOLDABLE FINS

[75] Inventor: Donald L. Harris, Miami Beach, Fla.

[73] Assignee: Cordis Leads, Inc., Miami, Fla.

[21] Appl. No.: 32,981

[22] Filed: Mar. 27, 1987

Related U.S. Application Data

[60] Continuation of Ser. No. 797,011, Jan. 21, 1986, abandoned, which is a division of Ser. No. 495,636, May 18, 1983, Pat. No. 4,585,013, which is a continuation-in-part of Ser. No. 225,703, Apr. 20, 1981, abandoned.

[51] Int. Cl.⁴ .............................................. A61N 1/05
[52] U.S. Cl. .................................... 128/785; 128/786; 128/419 P
[58] Field of Search ............................. 128/784–786, 128/419 P, 642

[56] References Cited

U.S. PATENT DOCUMENTS

| | | | |
|---|---|---|---|
| 3,087,486 | 4/1963 | Kilpatrick | 128/2.1 |
| 4,102,331 | 7/1978 | Grayzel et al. | 128/2.1 E |
| 4,198,991 | 4/1980 | Harris | 128/784 |
| 4,236,529 | 12/1980 | Little | 128/785 |
| 4,243,050 | 1/1981 | Littleford | 128/784 |
| 4,248,237 | 2/1981 | Kenny | 128/419 P |
| 4,269,198 | 5/1981 | Stokes | 128/785 |
| 4,301,815 | 11/1981 | Doring | 128/785 |
| 4,327,747 | 5/1982 | Gold | 128/784 |
| 4,409,994 | 10/1983 | Doring | 128/785 |

FOREIGN PATENT DOCUMENTS

| | | | |
|---|---|---|---|
| 2446001 | 1/1979 | France | 40/2 R |
| 7909050 | 6/1980 | Netherlands | 128/785 |
| 1219017 | 12/1968 | United Kingdom | 220/94 R |

*Primary Examiner*—Lee S. Cohen
*Attorney, Agent, or Firm*—Henry W. Collins; Thomas R. Vigil

[57] ABSTRACT

The finned pervenous lead electrically connects an electrical generator with an internal organ and comprises a flexible electrically conductive insulated lead with proximal and distal ends. The proximal end has an electrical connection for connecting the lead to the electrical generator and a distal electrode assembly connected to the distal end of said lead. A distal portion of the lead proximal to the distal electrode assembly has an axis and at least two tissue-engaging, thin, flexible, flat fins which are circumferentially sidewise deflectible and which project radially outwardly from different radial locations on the lead at about the same axial location on the lead. Each fin extends outwardly in a plane which includes the axis of the lead distal portion and each fin is attached to the lead at a fold line extending substantially parallel to the axis of the lead distal portion. Substantially an entire flat side of each of the fins is capable of folding circumferentially about the fold line against, contacting and conforming to the adjacent circumferential surface of the lead without overlapping when the fins are bent in the same sense around the lead and about the fold lines which define the hinges adjacent the lead.

The diameter of a cylindrical envelope defined by the fins on the lead and folded against the lead can thus be kept as small as possible and interference by the projecting fins with an introducer sheath through which the lead is fed into the vascular system can be reduced by manually twisting the lead about its axis to fold the fins at the fold lines around and against the circumferential surface of the lead in a non-overlapping manner.

10 Claims, 7 Drawing Figures

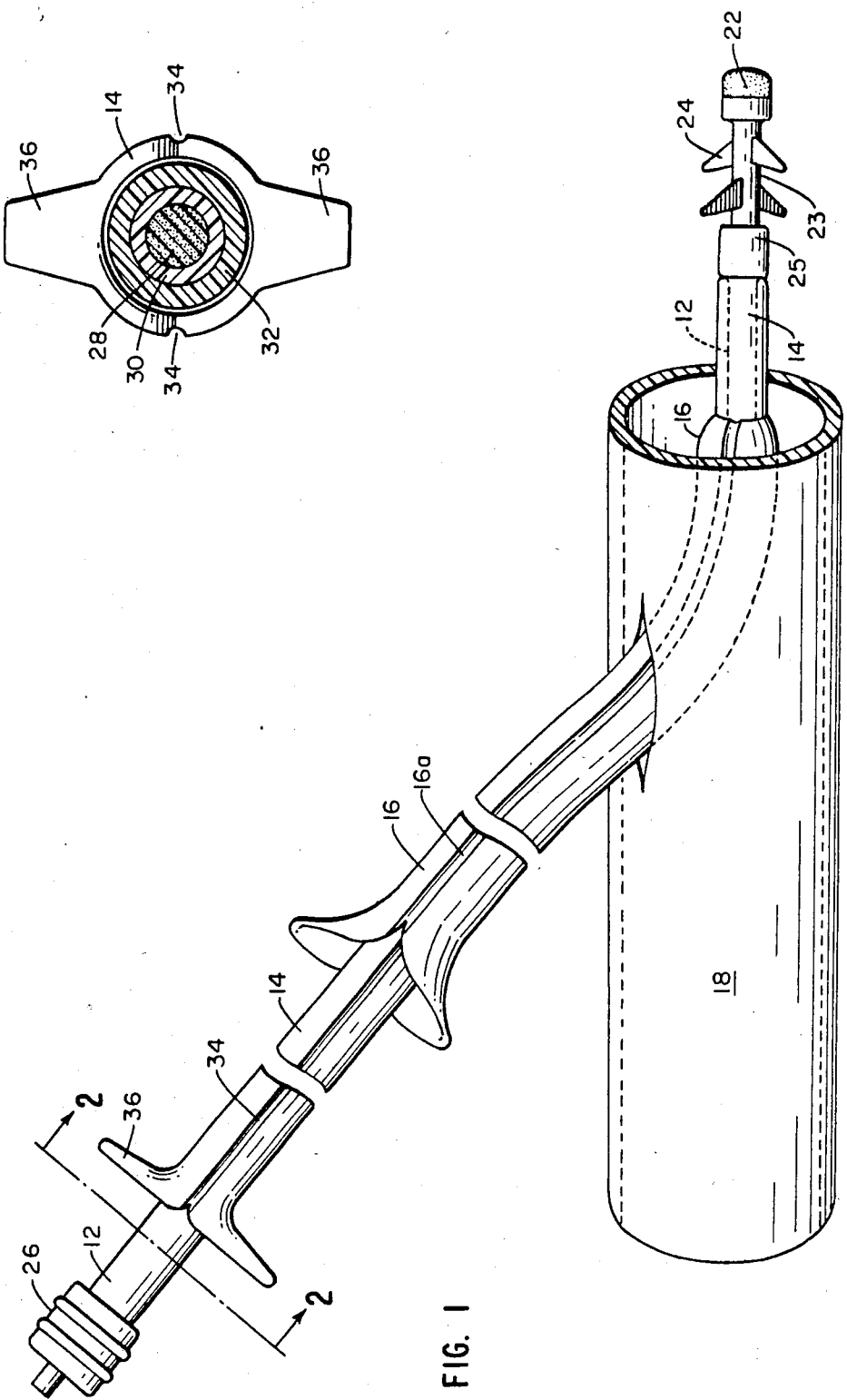

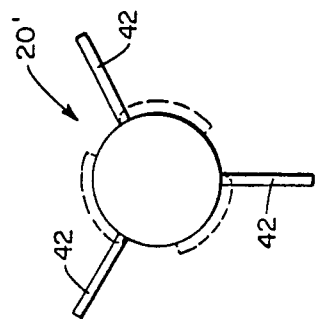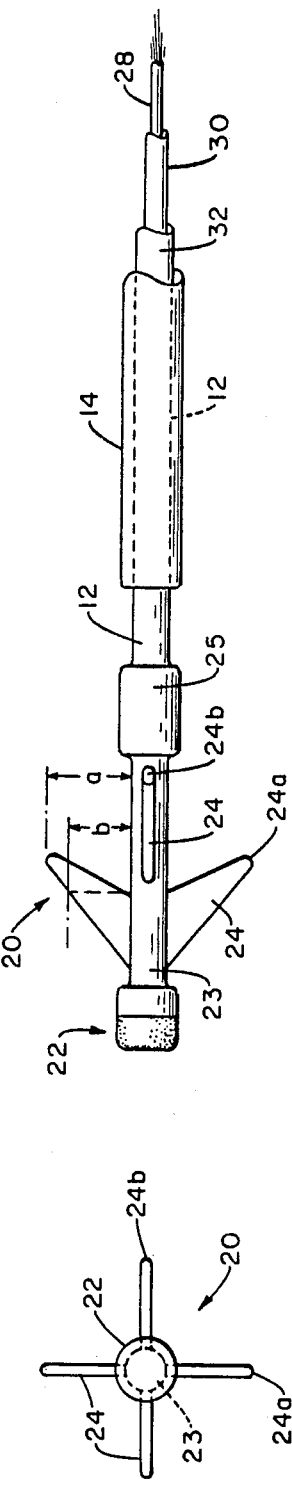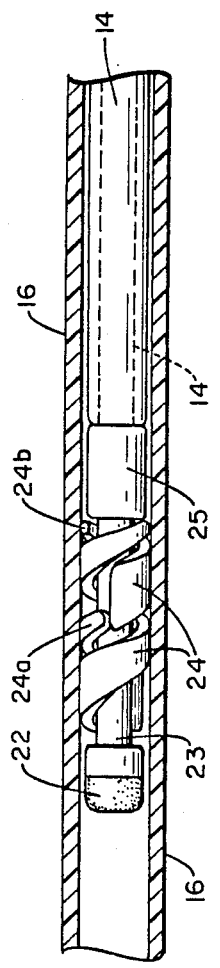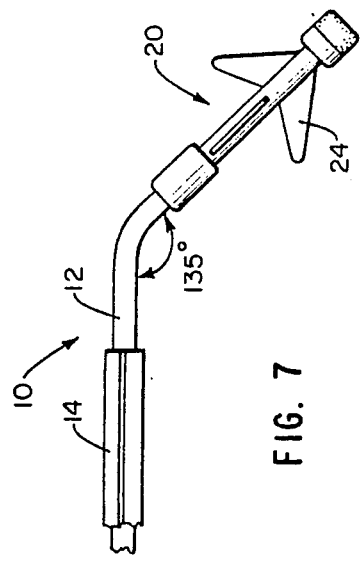

PERVENOUS ELECTRICAL PACING LEAD WITH FOLDABLE FINS

This is a continuation of application Ser. No. 797,011, filed Jan. 21, 1986, now abandoned, which is a division of application Ser. No. 495,636, filed May 18, 1983, now U.S. Pat. No. 4,585,013, issued on Apr. 29, 1986, which is a continuation-in-part of application Ser. No. 225,703, now abandoned.

BACKGROUND OF THE INVENTION

This invention relates to electrical leads, and more particularly to a lead which connects a source of electrical signals to an organ of the body such as the heart.

It is known to stimulate internal body organs such as the heart with electrical signals generated by an electronic device such as a pacemaker. These signals compensate for various cardiac dysfunctions such as rhythm disorders. Generally, the pacing device itself is located some distance away from the organ needing stimulation and is connected to the organ by an electrical lead.

One way of establishing electrode contact with heart muscle is to feed the electrode and its lead through the venous system into the heart. It is necessary in this case that the lead somheow be imparted with sufficient stiffness and maneuverability to negotiate the various turns encountered in the journey through the venous system to the heart. Once installed, the lead must have sufficient flexibility to withstand the continuous motion of the body over many years without undue mechanical stress. It is also desirable that a stimulating lead have small diameter to lessen interference with blood flow, to facilitate introduction into the vascular system and to accommodate multiple lead systems.

In the prior art, it is known to employ a lead with a central hole or lumen inside a long hollow coil of electrically conductive wire. A relatively stiff guide wire or stylet is inserted into the lumen as an aid for feeding the lead through the venous system. The stylet is fed through the lead all the way until it encounters the closed distal end of the lead. As the physician continues to push the proximal end of the stylet, the stylet transmits axial force to the electrode end of the lead. The lead in turn is driven, or actually pulled forward from the distal end. Observing the position of the end of the lead on a fluoroscope during the procedure, the physicial quickly "threads" the lead through the vascular system by manipulating the stylet from the outside. Physicians specializing in implantation of cardiac pacers, for example, are used to the foregoing procedure and have highly developed skills which enhance confidence in the procedure. The ease and familiarity of the stylet procedure also help reduce the trauma to the patient while insuring positive placement of the lead. Once the lead is installed, the stylet is removed. The remaining overall lead diameter, of course, is larger than would have been the case without the stylet-receiving lumen.

The electrodes on the distal ends of prior art cardiac stimulating leads are frequently equipped with protruding tines or fins to aid in attachment to the inside wall of the heart. These prior art electrodes were of relatively large diameter requiring a large diameter introducer sheath for entry into the vascular system. In addition, the need to restrict the overall diameter of the electrode required that the fins be kept small. Small fins, however, provide insufficient "anchoring".

It is, therefore, an object of the present invention to provide an extremely flexible stimulating lead with a reduced diameter while preserving stylet-like action during the implantation procedure.

It is a further object of the present invention to provide a lead having a distal tip of smaller diameter and longer fins without unduly increasing the overall diameter of the lead during introduction into the vascular system.

SUMMARY OF THE INVENTION

According to the present invention there is provided a finned pervenous lead for electrically connecting an electrical generator with an internal organ, comprising:

a flexible electrically conductive insulated lead with proximal and distal ends, said proximal end having means for electrically connecting said lead to the electrical generator, a distal electrode assembly connected to said distal end of said lead, a distal portion of said lead proximal to said distal electrode assembly having an axis and at least two tissue-engaging, thin, flexible, flat fins which are circumferentially sidewise deflectible and which project radially outwardly from different radial locations on the lead at about the same axial location on the lead, each fin extending outwardly in a plane which includes the axis of the lead distal portion and each fin being attached to said lead at a fold line extending substantially parallel to the axis of said lead distal portion, substantially an entire flat side of each of said fins being capable of folding circumferentially about said fold line against, contacting and conforming to the adjacent circumferential surface of the lead without overlapping when said fins are bent in the same sense around said lead and about said fold lines said distal portion of said lead in the area of said fins having a diameter less than the remainder of said lead whereby the diameter of a cylindrical envelope defined by said fins on said lead and folded against said lead can be kept as small as possible and no greater than the lead diameter during insertion or withdrawal of the lead and interference by the projecting fins with an introducer sheath through which the lead is fed into the vascular system can be reduced by manually twisting the smaller-in-diameter portion of said lead about its axis to fold the fins at said fold lines around and against the circumferential surface of the lead in a non-overlapping manner.

BRIEF DESCRIPTION OF THE DRAWING

The invention disclosed herein may be better understood with reference to the following drawing of which:

FIG. 1 is a diagrammatic representation of the lead disclosed herein being introduced into the vascular system via an introducer sheath;

FIG. 2 is a cross-sectional view of the lead system of FIG. 1 taken at lines 2—2;

FIG. 3 is a side view of the distal portion of the lead and guide sleeve of FIG. 1;

FIG. 4 is a front distal end view of the lead of FIG. 3;

FIG. 5 is a diagrammatic representation of the distal portion of the lead of FIGS. 1 and 3 being inserted through the introducer sheath with the fins wrapped around;

FIG. 6 is a diagrammatic representation of a front distal end view of another embodiment of the fins; and FIG. 7 is a diagrammatic representation of the lead of FIG. 1 with a preformed bend.

DESCRIPTION OF THE PREFERRED EMBODIMENT

In the embodiment of FIG. 1, a small diameter lumenless pervenous unipolar cardiac pacer lead system is designated generally at 10. The lead system 10 includes an insulated multifilament, small diameter, elongated, flexible lead body 12 surrounded by a guide sleeve 14. As illustrated, the lead system 10 is inserted through a conventional split sheath introducer 16 into a blood vessel 18 of the vascular system. The distal end of the lead body 12 terminates in an electrode assembly 20 (FIG. 3) which includes a distal electrode tip portion 22, an intermediate cylindrical body portion 23 of reduced diameter with four blade-like radial hooking fins 24, and a proximal annular enlargement forming a sleeve stop 25. The sleeve stop 25 and electrode tip 22 preferably have the same diameter as the outer diameter of the guide sleeve 14. The hooking fins are used to aid in attaching the electrode assembly 20 by snaring the trabeculae of the heart. Fibrotic growth also tends to envelop and ensnare the fins after implantation. Thr proximal end of the lead body 12 terminates in a connector 26 for a conventional cardiac pacer.

The multifilament lead body 12 has a diameter of approximately 0.053 inches which corresponds to a French 4 diameter. As shown in FIGS. 2 and 3, the lead body 12 is composed of a core 28 comrising a bundle of thousands of tiny carbon fibers (preferably 3000) in a high modulus graphite filament form. Suitable fiber material is available from the Union Carbide Corporation under the trademark "Thornel" and is designated as 300 WYP 30 1/0 with a special resin matrix added. Under this designation, the fibers are embedded in a resin matrix composed of tetrafluoroethylene mixed with a small proportion of urethane as described in U.S. Pat. No. 4,198,991, entitled "Cardiac Pacer Lead", the teachings of which are incorporated herein by reference. The core 28 is then pulled into a thin-walled tube 30 of polytetrafluoroethylene manufactured by Dupont and designated 6C having good lubricity and long flex life both to contain the fibers and to act as an electrical insulator. The combination of the tubing and resin matrix prevents the fibers from breaking or otherwise destroying one another as the lead 12 flexes both during introduction into the vascular system and thereafter during its intended operation. The core 28 and tube 30 assembly is next pulled into a body compatible polyurethane tube 32. A suitable tube 32 material is available from Mobay Chemical Corporation of Pittsburgh, Pennsylvania under the designation Texin 85-A. The polyurethane tube 32 is first allowed to expand in chlorothene for fifteen to thirty minutes before being pulled over the core 28-tube 30 assembly. The polyurethane tube 32 is then allowed to shrink by exposure to air. The lead body 12 is thus of solid construction since a lumen is not needed as in the prior art systems which use an internal stylet to guide the lead to the heart.

The multifilament lead body 12 is surrounded by the guide sleeve 14 which is adapted to impart axial force to the distal end to drive the lead 12 through the vascular system. The sleeve 14 is a substantially cylindrical jacket preferably made of a high density polyethylene such as Marlex HHM 4903 available from Phillips Petroleum, and compounded with approximately 10% barium sulphate and 1% titanium dioxide to make the sheath radiopaque and white. The sleeve 14 slides over the lead body 12 at the time that the lead system 10 is manufactured. Thus is comes "built-on" the lead. The sleeve 14 has a wall thickness of approximately 0.0065 inch, so that the combined lead body 12 and sleeve 14 diameter is approximately 0.066 inches corresponding to a French 5 diameter. Because the inner diameter of the sleeve 14 is less than or equal to the cross-sectional diameter of the sleeve stop 25 of the electrode assembly 20 diameter (approximately 0.079 inch), the sleeve 14 acts as a pusher for guiding the electrode assembly 20 to the target organ. After the sleeve 14 is assembled onto the lead body 12, the electrode assembly 20 and connector 26 are affixed to the distal and proximal ends of the lead respectively in an electrically conducting relation in the manner described in the above-mentioned U.S. Pat. No. 4,198,991.

The guide sleeve 14 serves only to drive the lead through the vascular system to the target organ; it must be removed once the electrode assembly 20 is properly positioned. It cannot be removed by sliding it off because its diameter is much smaller than that of the connector 26 over which it would have to be removed. (It could be removed by sliding it from the lead body 12 if the connector 26 were not attached to the lead until the lead had been positioned within the body. However, the connector 26 then would have to be attached to the lead in the midst of a sterile procedure, a practical impossibility.) A similar problem is encountered in removing the short introducer sheath 16 (FIG. 1). As explained in U.S. Pat. No. 4,166,469 to Littleford, the introducer sheath is equipped with means defining longitudinal weakening lines 16a so that the introducer can be split and peeled apart to remove it from the lead. According to the present invention, the guide sleeve 14 is also rendered readily removable by providing it with longitudinally extending separating grooves 34 over its entire length, i.e. substantially the length of the lead. The sleeve 14 can be peeled apart by grasping the handles 36 and pulling gently. The handles 36 are molded onto the sheath 14. The grooves 34 are approximately 0.005 inch deep which represents an 80% to 90% cut through the wall of the sheath 14. Such a groove assures that the sleeve 14 will separate readily. As shown in FIG. 1, during introduction into the vessel, the lead 12 is surrounded by two split "sheaths", the long guide sleeve 14 and the short introducer 16.

The electrode assembly 20 comprises the electrode tip portion 22 which is adapted for engaging the organ to be stimulated in an electrically conducting relationship. The electrode 22 is of conventional design with a diameter of approximately 0.079 inch and may be porous or nonporous. A suitable material is elgiloy or platinum, or even an extension of the carbon fibers themselves. At the other end of the electrode body 23, the sleeve stop 25 halts the forward motion of the sleeve 13 in relation to the lead 12. By preventing further forward motion of the sleeve 14 independent of the lead, the sleeve stop 25 forces the sleeve 14 to push the electrode assembly 20 through the venous system to the heart.

The electrode assembly 20 is specifically adapted to anchor the tip fo the lead inside the heart. The hooking fins 24 become ensnared in the fine tangled trabeculae of the heart wall to immobilize the electrode assembly 20 with respect to the heart muscle. The four blade-like fins 24 (FIGS. 3 and 4) are made of a thin, flexible material such as silastic or polyurethane. When the lead is twisted, the fins 24 fold circumferentially without overlap and the diameter is small enough so that it may be inserted through an introducing assembly used for a French 7 diameter lead (FIG. 5). Once the electrode assembly 20 has passed through the introducing assembly 16, the resilient fins 24 resume their deployed state.

As shown in FIGS. 3 and 4, the preferred staggered fin arrangement comprises a first pair of opposed coplanar fins at 0° and 180° with respect to the orientation of the first fin about the lead body axis and a second pair of opposed coplanar fins at 90° and 270° axially spaced from the first pair. By design the fins' deployed radial length is about three-fourths of a circumference, expressed as $a = 3/2(\pi r)$, where r is the radius of the lead body 23. To avoid overlapping the opposed fin of the same pair, the distance b, i.e., the radial extent of the fin from the rear attachment point of the fin to the lead body must be less than a half circumference or $b < \pi r$. This relationship governs the angle of the fin. The first fin in the second pair is attached to the lead body 23 jut beyond the point reached by the tip 24a (FIG. 5) of the corresponding fin of the first pair when it is wrapped flat around the lead body. Other geometries are possible. For example, one long fin could be used at each of three axially spaced locations. To avoid overlapping itself, the pitch of the larger fin would be confined to $b < \pi r$. Each fin, when extended, is flat and parallel to the lead axis. Thus each fin is attached to the cylindrical lead body 23 at a line substantially parallel to the axis.

In the alternate simpler embodiment of FIG. 6, three fins are equally circumferentially spaced at the same axial location and each has a length just under one-third of the circumference of the lead body to avoid overlap. In very small diameter leads, however, this length may offer inadequate anchoring.

In operation, the small diameter lead system 10 is introduced through the sheath 16 into a vessel 18 in FIG. 1. Once the lead has been introduced as shown in FIG. 1, the sheath 16 can be removed by peeling it apart along lines 16a as it is pulled out of the blood vessel. The lead with its electrode assembly 20 is guided through the vascular system by means of the stylet-like action of the external guide sleeve 14.

When the ventricle of the heart is the target organ, the lead must pass through the tricuspid valve of the heart. Because of the location of the tricuspid valve, it is helpful for the distal end of the lead to have a pronounced bend in it so that it can more easily pass through the valve. In prior art devices the removable internal stylet itself was bent to enable passage through the tricuspid valve. In the present embodiment, however, since there is no internal stylet, a portion of the carbon lead body 12 itself about 5 cm. from the distal end of the tip 22 has a pre-formed 135° bend, as shown in FIG. 7. This pre-formed bend is created by heating the lead body 12 in a form so that the tubing over the fibers will take a set upon cooling. While the sleeve 14 covers this pre-formed portion, however, the lead body 12 is straightened. At the tricuspid valve, the sleeve 14 is retracted from the electrode assembly 22 by means of the handles 36 so that the bend in the carbon lead 12 is deployed to navigate the passage through the tricuspid valve. Once the distal portion of the lead has assumed the proper position, the sleeve 14 is advanced to the sleeve stop 25, covering the bend in the lead 12 again to straighten it for its final positioning within the heart.

At the desired location, the hooking fins 24 engage the trabeculae of the heart. After the electrode assembly is securely in place, the sleeve 14, having performed its function of driving the lead to the target organ, is peeled apart as it is withdrawn from the vessel 18 (FIG. 1). The carbon lead body 12 and the electrode assembly 20 remain in the body. With time, fibrotic tissue further ensnares the electrode assembly 20 thus securing the distal end of the lead. If it is desired to remove the lead at some later time, the lead may be twisted to help free the electrode assembly 20 by wrapping the fins around the electrode so that it can be repositioned or withdrawn.

The unipolar embodiment shown in the drawings may be modified to provide a small diameter bipolar lead by interposing a suitable hollow, coaxial conductor (e.g., coiled elgiloy) between the tubes 30 and 32 and placing an electrically connected ring electrode on the sleeve stop 25.

Thus the invention provides a small diameter lumenless lead retaining stylet-like action to aid in its journey through the venous system. The use of the external sleeve eliminates the need for the lead itself to have a hollow interior to accommodate a stylet as known in prior art systems, thereby reducing the overall diameter of the lead. The reduced size is particularly advantageous in multiple lead systems. The carbon filament core procies increased flexibility. In addition, the non-overlapping folding fin design allows proportionately larger fins without increasing the diameter of the electrode assembly as it passes through the introducer sheath thus minimizing trauma to the patient.

Although this invention has been described with reference to specific embodiments, it is understood that modifications and variations may occur to those skilled in the art. It is intended that all such modifications and variations be included within the scope of the appended claims.

What is claimed is:

1. A finned pervenous lead for electrically connecting an electrical generator with an internal organ, comprising:

a flexible electrically conductive insulated lead having a first preselected lead diameter and proximal and distal ends, said proximal end having means for electrically connecting said lead to the electrical generator, a distal electrode assembly connected to said distal end of said lead, said distal electrode assembly including a distal electrode tip portion having a second preselected diameter slightly in excess of the lead diameter, an intermediate body portion proximal to said distal electrode tip having a third preslected diameter which is less than the electrode tip diameter, an axis and at least two tissue-engaging, thin, flexible, flat fins which are circumferentially sidewise deflectible and which project radially outwardly from different radial locations on said intermediate body portion at about the same axial location on said intermediate body portion, each fin extending outwardly in a plane which includes the axis of said intermediate body portion and each fin being attached to said intermediate body portion at a fold line extending substantially parallel to the axis of said intermediate body portion, substantially an entire flat side of each of said fins being capable of folding circumferentially about said fold line against, contacting and conforming to the adjacent circumferential surface of said intermediate body portion without overlapping when said fins are bent in the same sense around said intermediate body portion and about said fold lines whereby the diameter of a cylindrical envelope defined by said fins on said lead and folded against said intermediate body portion can be kept as small as possible and no greater than substantially the outer diameter of a French 7 lead during insertion withdrawal after deployment to project radially of the lead and interference by the projecting fins with an introducer sheath through which the lead is fed into the vascular system can be reduced by manually twisting the lead about its axis to fold the fins at said fold lines around and against the circumferential surface of the intermediate body portion in a non-overlapping manner.

2. The lead of claim 1, wherein the axial locations of said two fins are staggered along said intermediate body portion.

3. The lead of claim 1, wherein said at least two fins comprise a first pair of fins which, when deployed, extend in opposite directions from approximately the same first axial location along said intermediate body portion and lie approximately in the same first plane including the axis of said intermediate body portion and said intermediate body portion includes a second pair of fins which, when deployed, extend in opposite directions from approximately the same second axial location spaced from the first and lie approximately in the same second plane including the axis of said intermediate body portion.

4. The lead of claim 3, wherein the axial displacement between the first and second pairs of fins and the angle between the first and second planes is determined by the length of the fins of the first pair so as to minimize the spacing between the first and second pairs of fins while avoiding any overlap when the fins are folded.

5. The lead of claim 3, wherein said first and second planes are approximately orthogonal.

6. The lead of claim 1 including one or more additional fins, all of said fins extending in different radial directions from the same axial location of said intermediate body portion, the length of each fin corresponding to the circumferential spacing between adjacent fins to permit non-overlapping folding of the fins when the lead is manually twisted during introduction thereof.

7. The lead of claim 1, wherein said fins extend from opposite sides of said intermediate body portion and lie in the same plane.

8. The lead of claim 1, including third and fourth fins attached to said intermediate body portion at about the same axial location which location is spaced axially rearwardly of the axial location of said first named fins and each of said third and fourth fins extending radially outwardly from said intermediate body portion in planes which include the axis of the intermediate body portion but which are not coplanar with the plane of either said first named fin or said second named fin, and all of said fins having a shape and an extent and being positioned on said lead such that, when the fins are folded circumferentially about said intermediate body portion and against the circumferential surface of said intermediate body portion upon twisting of the lead, said fins do not overlap each other.

9. The lead of claim 1, including a third fin which is substantially identical to said first named fins and which is attached to said intermediate body portion about a fold line extending substantially parallel to the axis of said intermediate body portion, and all three fins being circumferentially spaced about said intermediate body portion approximately 120° from each other and each having a shape and extent and being positioned on said intermediate body portion such that, when said fins are folded circumferentially about said intermediate body portion and against the circumferential surface of said intermediate body portion upon twisting of the lead, said fins do not overlap each other.

10. The lead of claim 1, including a third fin spaced axially rearwardly from said first named fins and attached to said intermediate body portion, said third fin lying in a plane which includes the axis of the intermediate body portion but which is not coplanar with the plane of either of the first named fins and all three fins having a shape and extent and being positioned on said intermediate body portion such that, when said fins are folded circumferentially about said intermediate body portion and against the circumferential surface of said intermediate body portion upon twisting of the lead, said fins do not overlap each other.

* * * * *